United States Patent [19]

Chiodo et al.

[11] Patent Number: 4,658,821
[45] Date of Patent: Apr. 21, 1987

[54] EJECTOR FOR AN AUTOMATIC LANCET ARM

[75] Inventors: Daniel J. Chiodo; Joseph Maggio, both of Hialeah, Fla.

[73] Assignee: Packaging Corporation International a/k/a/ Medicore, Hialeah, Fla.

[21] Appl. No.: 908,928

[22] Filed: Sep. 15, 1986

Related U.S. Application Data

[63] Continuation of Ser. No. 817,079, Jan. 8, 1986, abandoned.

[51] Int. Cl.⁴ .............................................. A61B 17/34
[52] U.S. Cl. .................................. 128/314; 128/329 R
[58] Field of Search .................. 128/314, 315, 329 R, 128/330, 637, 751-755; 604/22, 46, 47

[56] References Cited

U.S. PATENT DOCUMENTS

| | | |
|---|---|---|
| 585,007 | 6/1897 | Rambaud . |
| 741,886 | 10/1903 | Chandler . |
| 786,358 | 4/1905 | Houghton . |
| 866,995 | 9/1907 | Wright . |
| 3,358,689 | 12/1967 | Higgins .............................. 128/329 |
| 4,230,118 | 10/1980 | Holman et al. ..................... 128/314 |

FOREIGN PATENT DOCUMENTS 869846  3/1953  Fed. Rep. of Germany ...... 128/314

Primary Examiner—Michael H. Thaler
Attorney, Agent, or Firm—Oltman and Flynn

[57] ABSTRACT

The present invention consists of an improvement on the pivoting arm of an automatic lancet. Generally an automatic lancet is comprised of a housing having a spring loaded pivoting arm. The arm has a cylindrical holder at the operating end which holds a needle encased in a plastic carrier. Upon releasing the spring, the needle pierces the patient's finger producing a blood sample. To replace the needle generally requires pulling the old needle out with one's fingers and pushing a new one in. The present invention improves the cylindrial holder by adding a plunger inside it. This enables the user to push the old needle out without the necessity of grabbing or touching the old needle. Thus, safety for the medical technician is greatly enhanced.

1 Claim, 9 Drawing Figures

EJECTOR FOR AN AUTOMATIC LANCET ARM

This application is a continuation, of application Ser. No. 817,079, filed Jan. 8, 1986 now abandoned.

FIELD OF THE INVENTION

The present invention relates to an improvement of a medical instrument known as an automatic lancet. The automatic lancet has a spring loaded small needle used to prick the finger to obtain a blood sample.

BACKGROUND OF THE INVENTION

U.S. Pat. No. 4,230,118 to Holman et al. has become a generally accepted medical instrument used to prick the finger to obtain a blood sample. A housing contains a spring loaded pivoting arm which has a cylindrical holder at its operating end. The holder holds a small needle which is housed in a plastic carrier. Pushing a trigger releases the arm holding the needle. The needle pricks the finger from which the blood sample is taken. Presently the user must grab the exposed sharp needle and its surrounding carrier and pull the used needle out of the holder before inserting a new needle. This procedure poses the risk of having the medical technician accidentally pricking his fingers on the used needle thus introducing the patient's blood directly into his own blood stream. This direct introduction of a patient's blood into the medical technician's blood poses serious health hazards to the medical technicians.

SUMMARY OF THE INVENTION

It is, therefore, the primary object of the present invention to provide an improvement to the automatic lancet whereby the addition of a plunger inside the needle holder allows the medical technician to remove a used needle from the holder by pushing the plunger, thus avoiding any contact with the used needle.

Other objects of this invention will appear from the following description and appended claims, reference being had to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE DRAWINGS

Figure 1:
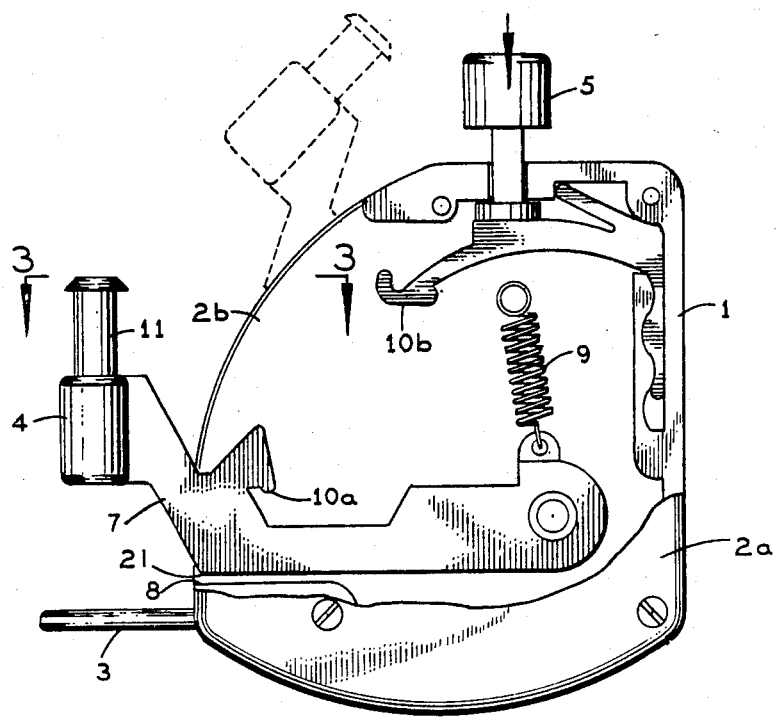
FIG. 1 is a left side elevational view partially cut away showing the working parts of the automatic lancet.

Referring first to FIG. 1, automatic lancet 1 is comprised of a housing having parts 2A and 2B. In operation, detachable finger rest 3 is placed on top of the patient's finger (not shown). Pivot arm 7 is cocked back to the position shown in dotted lines. Trigger 5 is pressed to release pivot arm 7 forcefully against stopper 8. Pivot arm 7 slides in groove 6. Spring 9 supplies the pivoting force to pivot arm 7 when couplings 10A and 10B are uncoupled by depression of trigger 5. The action end of pivot arm 7 is comprised of holder 4. The present invention is comprised solely of plunger 11 inside holder 4, and the modification of holder 4 to include a hole on top for the plunger 11.

Figure 2:
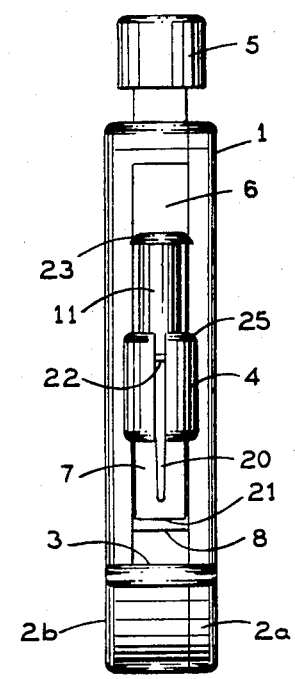
FIG. 2 is a front elevational view of the automatic lancet showing the improved lancet holder having a plunger.

FIG. 2 shows the pivot arm 7 in a neutral position midway along groove 6. After cocking and upon actuation of trigger 5, the base 21 of pivot arm 7 slams into stopper 8. Arm 7 then retracts slightly to the neutral position. Holder 4 has a center groove 20 which expands to hold the needle (see FIGS. 7, 8 and 9). The top 25 of holder 4 is contoured inward providing an inside collar in holder 4 (see FIG. 4). Plunger 11 has a matching flange 22 which prevents plunger 11 from falling out of holder 4. Outer flange 23 on plunger 11 prevents plunger 11 from falling through holder 4.

Figure 3:
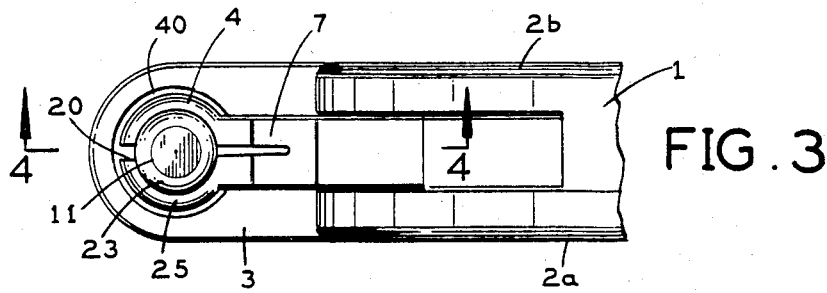
FIG. 3 is a partial top plan view of the automatic lancet taken along line 3—3 of FIG. 1 showing the pivoting arm.

FIG. 3 shows how outer flange 23 on plunger 11 rests against the top 25 of holder 4.

Figure 4:
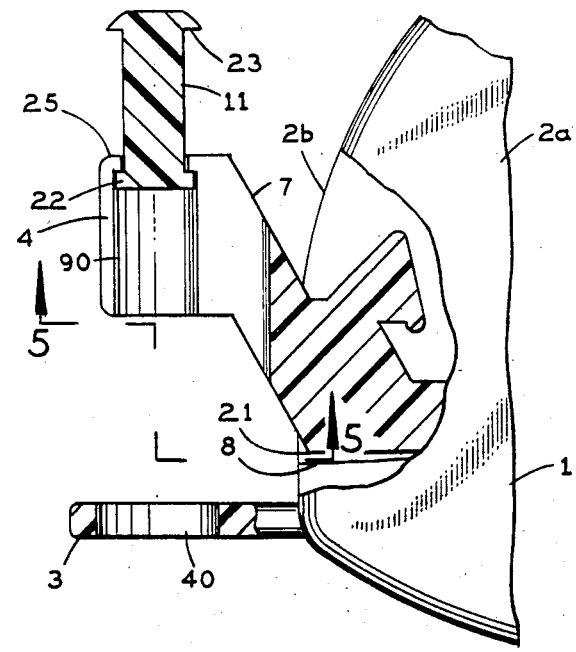
FIG. 4 is a fragmentary sectional view of the pivoting arm taken along line 4—4 of FIG. 3.
Figure 8:
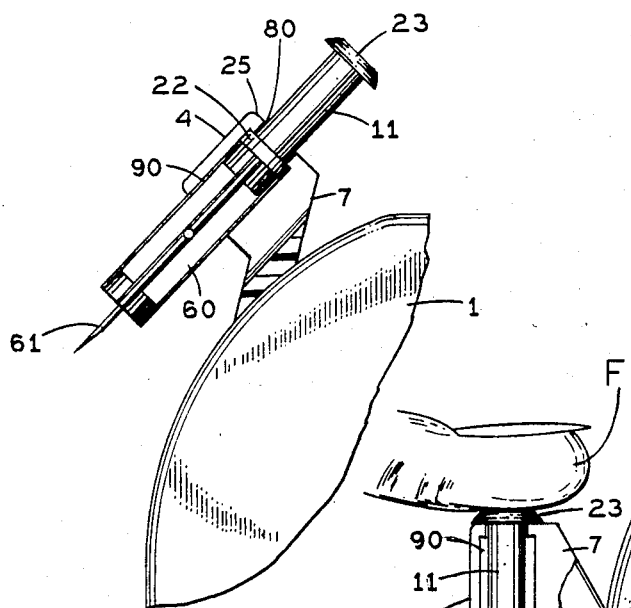
FIG. 8 is a left side fragmentary sectional view of the automatic lancet showing the lancet needle in its carrier snugly fit against the plunger.

FIG. 4 shows how holder 4 lines up with hole 40 in finger rest 3. FIG. 8 shows how the lancet needle fits in arm 7. Flange 22 abuts against holder top 25 and plunger 11 is thereby held slidingly engaged within holder 4. Flange 22 slidingly engages the cylindrical center 90 of holder 4.

Figure 5:
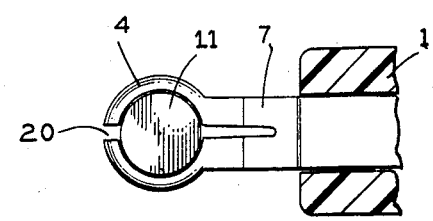
FIG. 5 is a partial bottom plan view of the automatic lancet taken along line 5—5 of FIG. 4 showing the pivoting arm.

FIG. 5 shows the bottom of plunger 11 held inside holder 4.

Figure 6:
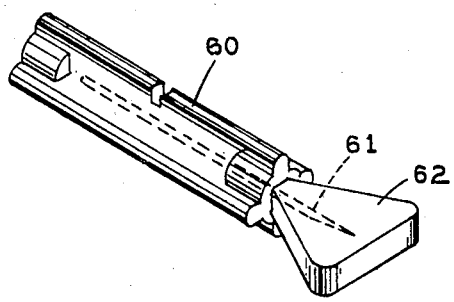
FIG. 6 is a top perspective view of a lancet needle shown in dotted lines still encased in a protective tip.

FIG. 6 shows needle 61 in dotted lines encased in protective tip 62. Protective tip 62 is twisted off before use. Ribbed carrier 60 securely holds needle 61.

Figure 7:
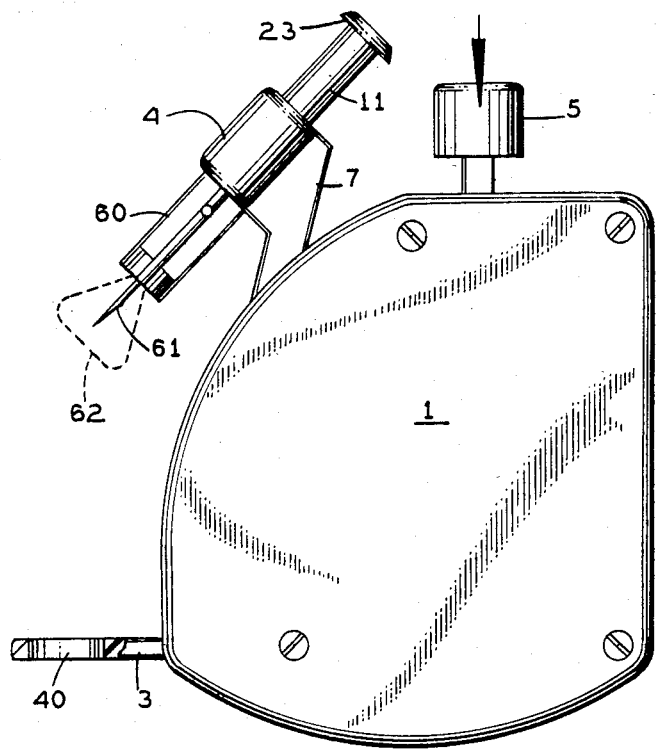
FIG. 7 is a left side elevational view of the automatic lancet cocked and ready to be actuated.

FIG. 7 shows needle assembly 60, 61 and 62 mounted in operating position inside holder 4. Pivot arm 7 is in the cocked position whereby depressing trigger 5 would propel needle 61 through hole 40 into a patient's finger (not shown).

FIG. 8 shows how holder 4 has a hole 80 on top which guides plunhger 11. Plunger flange 22 also guides plunger 11 down the cylindrical center 90 of holder 4 when plunger 11 is depressed in order to eject needle assembly 60, 61. Ribbed carrier 60 fits securely inside the cylindrical center 90 of holder 4 during operation.

Figure 9:
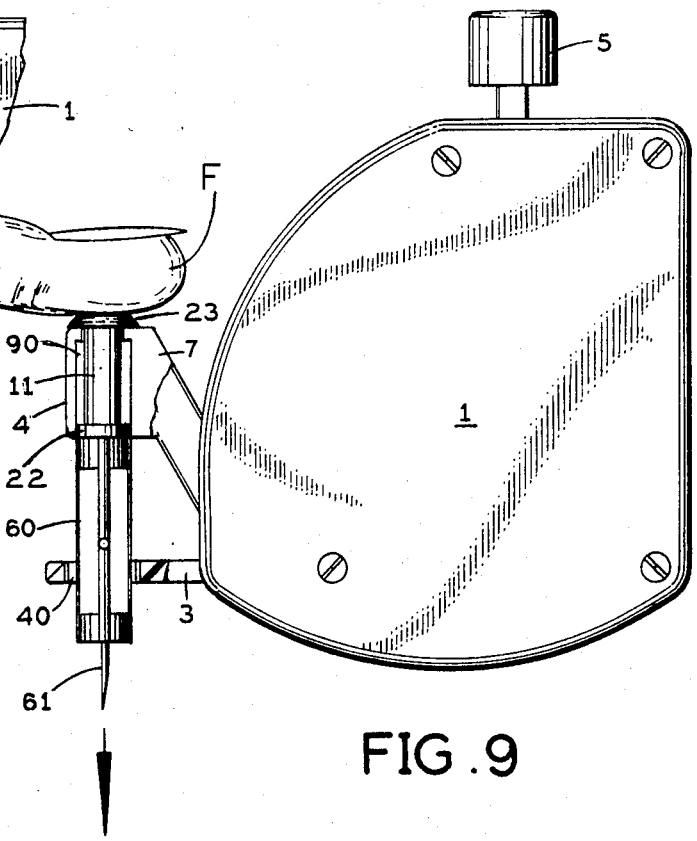
FIG. 9 is a left side elevational view of the automatic lancet with a fragmentary sectional view of the lancet holder during ejection.

FIG. 9 shows a medical technician's finger F depressing plunger 11 thereby ejecting needle assembly 60, 61 through hole 40 in finger rest 3. During ejection, pivot arm 7 would normally be in the neutral position after use as shown. The medical technician is protected from accidental pricking during insertion of a new needle assembly 60, 61, 62 because protective tip 62 is still in place (not shown).

I claim:

1. In combination with a lancet device comprising:

a housing;

an arm mounted in the housing for movement between a retracted position and an operating position, said arm having an end outside said housing;

a holder on said end of the arm, said holder having a recess therein which is open at one end for the slidable insertion and removal of a lancet needle assembly, said holder having an end wall with an opening therein at the opposite end of said recess;

spring means urging said arm from said retracted position to said operating position;

and manually releasable latch means for holding said arm in said retracted position against the urging of said spring means;

a plunger having a peripheral flange slidably received in said recess in the holder, said plunger extending from said flange slidably through said opening in said end wall to the outside of said holder for manual actuation;

and a lancet needle assembly slidably received in said recess in the holder, said lancet needle assembly at one end presenting a needle located beyond said open end of said recess in the holder and at its opposite end positioning said flange on the plunger against said end wall of the holder;

said plunger being slidable toward said one end of the recess to push the lancet needle assembly out of said recess in the holder.

* * * * *